US008395398B2

(12) United States Patent
Xu et al.

(10) Patent No.: US 8,395,398 B2
(45) Date of Patent: Mar. 12, 2013

(54) METHOD OF CHARACTERIZING PARTICLES

(75) Inventors: Renliang Xu, Pembroke Pines, FL (US); Yiming Yang, Ichigawa (JP)

(73) Assignee: Beckman Coulter, Inc., Brea, CA (US)

( * ) Notice: Subject to any disclaimer, the term of this patent is extended or adjusted under 35 U.S.C. 154(b) by 501 days.

(21) Appl. No.: 12/766,057

(22) Filed: Apr. 23, 2010

(65) Prior Publication Data

US 2010/0271053 A1    Oct. 28, 2010

Related U.S. Application Data

(60) Provisional application No. 61/172,491, filed on Apr. 24, 2009.

(51) Int. Cl.
*G01R 27/08* (2006.01)
(52) U.S. Cl. ........ 324/699; 324/71.4; 324/71.1; 377/11; 377/12; 702/21; 702/26; 702/29
(58) Field of Classification Search .................. 324/699, 324/71.4, 71.1; 377/11, 12; 702/21, 26, 702/29
See application file for complete search history.

(56) References Cited

U.S. PATENT DOCUMENTS

| 2,097,760 | A | * | 11/1937 | Gloacchino | .................... | 378/53 |
| 2,656,508 | A | * | 10/1953 | Coulter | ........................ | 324/71.1 |
| 2,985,830 | A | * | 5/1961 | Coulter et al. | ............... | 324/71.1 |
| 3,259,842 | A | * | 7/1966 | Coulter et al. | ................. | 377/12 |
| 3,413,545 | A | * | 11/1968 | Whitby | ........................ | 324/71.1 |
| 3,648,758 | A | * | 3/1972 | Kreuz et al. | ............... | 164/155.7 |
| 3,657,725 | A | * | 4/1972 | Estelle et al. | .................. | 377/12 |
| 3,665,295 | A | * | 5/1972 | Schoen | ........................ | 324/450 |
| 3,769,582 | A | * | 10/1973 | Schoen | ........................ | 377/12 |
| 3,771,058 | A | * | 11/1973 | Hogg | ........................... | 324/71.1 |
| 3,781,675 | A | * | 12/1973 | Angel | ......................... | 324/71.1 |

(Continued)

FOREIGN PATENT DOCUMENTS

EP    0510788 A2    10/1992

OTHER PUBLICATIONS

ISO—International Standard "Determination of particle size distributions—Electrical sensing zone method" First Edition Apr. 1, 2000, ISO 13319:2000(E).

*Primary Examiner* — Patrick Assouad
*Assistant Examiner* — Lamarr Brown
(74) *Attorney, Agent, or Firm* — Merchant & Gould P.C.

(57) ABSTRACT

Mixtures containing homogeneously-sized particles with a minimum concentration of agglomerates or larger particles are desired in various manufacturing processes such as, for example, in the manufacture and use of chemical mechanical polishing slurries, food emulsions, pharmaceutical products, paints, and print toner. The method disclosed herein provides these industries with an accurate and efficient method of screening such mixtures for such agglomerates and large particles. The method generally includes preparing a suspension of the mixture in an electrolyte, wherein the suspension includes a specified concentration of small particles per unit of electrolyte. The method further includes passing the prepared suspension, and a plurality of the particles therein, through an aperture of a device capable of characterizing particles according to the Coulter principle to obtain data on the particles. Still further, the method includes deriving a particle size distribution of the large particles from the obtained data. The suspension includes at least one small particle per aperture volume. The large particles have an average diameter that is at least five times greater than the average diameter of the small particles. The aperture has a diameter that is (i) at least 50 times greater than the average diameter of the small particles, and (ii) about 1.2 times greater than the average diameter of the large particles to less than about 50 times greater than the average diameter of the large particles.

16 Claims, 8 Drawing Sheets

U.S. PATENT DOCUMENTS

| | | | |
|---|---|---|---|
| 3,810,010 A * | 5/1974 | Thom | 324/71.1 |
| 3,949,198 A * | 4/1976 | Coulter et al. | 377/12 |
| 4,078,211 A * | 3/1978 | Longman, Jr. | 324/71.1 |
| 4,090,129 A * | 5/1978 | Gear | 324/71.1 |
| 4,103,229 A * | 7/1978 | Gear | 324/71.1 |
| 4,161,690 A * | 7/1979 | Feier | 324/71.4 |
| 4,853,618 A * | 8/1989 | Holley | 324/71.4 |
| 5,098,657 A * | 3/1992 | Blackford et al. | 422/73 |
| 5,274,431 A * | 12/1993 | Kuroda | 356/36 |
| 5,402,062 A * | 3/1995 | Barnes et al. | 324/71.4 |
| 5,432,992 A * | 7/1995 | Barnes et al. | 29/525 |
| 5,500,992 A * | 3/1996 | Barnes et al. | 29/525 |
| 6,052,184 A | 4/2000 | Reed | 356/338 |
| 6,111,398 A * | 8/2000 | Graham | 324/71.4 |
| 6,175,227 B1 * | 1/2001 | Graham et al. | 324/71.4 |
| 6,228,652 B1 * | 5/2001 | Rodriguez et al. | 436/63 |
| 6,259,242 B1 * | 7/2001 | Graham et al. | 324/71.4 |
| 6,624,621 B2 | 9/2003 | North, Jr. | |
| 6,873,725 B2 * | 3/2005 | Xu | 382/154 |
| 7,060,203 B2 * | 6/2006 | Shiba | 252/408.1 |
| 7,457,709 B2 * | 11/2008 | Zhang et al. | 702/26 |
| 7,609,369 B2 * | 10/2009 | Simon-Lopez | 356/39 |
| 8,154,273 B2 * | 4/2012 | Britton et al. | 324/71.4 |
| 8,247,214 B2 * | 8/2012 | Sowerby et al. | 435/283.1 |
| 2001/0052763 A1 * | 12/2001 | North, Jr. | 324/71.4 |
| 2002/0079225 A1 * | 6/2002 | Shiba | 205/81 |
| 2003/0013083 A1 * | 1/2003 | Tsai et al. | 435/5 |
| 2004/0004717 A1 * | 1/2004 | Reed | 356/338 |
| 2004/0047502 A1 * | 3/2004 | Xu | 382/154 |
| 2007/0143033 A1 * | 6/2007 | Zhang et al. | 702/26 |
| 2007/0194775 A1 * | 8/2007 | Ahn | 324/71.4 |
| 2007/0205747 A1 * | 9/2007 | Cho et al. | 324/71.4 |
| 2007/0212628 A1 | 9/2007 | Ishikawa | |
| 2008/0319680 A1 * | 12/2008 | Fox et al. | 702/21 |
| 2009/0315533 A1 * | 12/2009 | Atchley et al. | 324/71.4 |
| 2010/0021883 A1 * | 1/2010 | Sowerby et al. | 435/6 |
| 2010/0090677 A1 * | 4/2010 | Britton et al. | 324/71.1 |

\* cited by examiner

PARTICLE SIZE DISTRIBUTION

FIG. 8

METHOD OF CHARACTERIZING PARTICLES

CROSS-REFERENCE TO RELATED APPLICATION

The benefit under 35 U.S.C. §119(e) of U.S. Provisional Application Ser. No. 61/172,491 filed Apr. 24, 2009, the disclosure of which is incorporated herein by reference, is hereby claimed.

BACKGROUND

1. Field of the Disclosure

The disclosure generally relates to a method of characterizing particles according to the Coulter principle and, more specifically, to a method of characterizing large particles present among a mixture of predominantly uniform-sized smaller particles.

2. Brief Description of Related Technology

Liquid suspensions of sized particles are useful in many industries. These liquids often are of great benefit when the sized particles are homogenous, preferably in terms of size and weight. For example, chemical mechanical planarization is a liquid flow application traditionally used in glass polishing, and commonly used today in the manufacture of semiconductors. Chemical mechanical planarization (CMP) applications employ slurries to polish silicon wafers and provide uniform, scratch-free surfaces for fabrication of semiconductor devices. These slurries are often prepared in a central location, mixed, and then conveyed through distribution lines and dispensed to equipment suitable for polishing surfaces. These slurries are generally made up of polydisperse colloidal or fumed abrasive particles. Importantly, these slurries often contain very fine particles up to 0.2 micrometers (μm) in size. Larger size particles (e.g., 1 μm or greater) are often present in the slurries at a process point where the slurry is dispensed for polishing. These larger particles may have been formed as a result of shearing, agglomeration, or due to the presence of a foreign material in the slurry. The agglomerated slurry particles present during polishing are undesirable and can cause many defects in the wafer such as, for example, scratches due to deep indentation or non-uniform polishing due to differential polishing pressure. The presence of agglomerated particles can be minimized by carefully milling the fine particles, continuously mixing the slurry upstream of its distribution, maintaining a proper electrolyte balance, and employing filters at dispensation points to remove the agglomerates before the slurry is delivered to the wafer.

The desirability of homogeneously-sized particles with a certain, minimized concentration of agglomerates is certainly not limited to CMP applications. To the contrary, this desirability extends to various other applications. For example, in the pharmaceutical industry, agglomerates and disparately-sized particles are undesired in pharmaceutical preparations that must include accurate and reproducible doses of active substances. These particles can include proteins, which may tend to agglomerate when in solution. Agglomeration can affect the activity and stability of the proteins, therefore the pharmaceutical industry needs to know whether solutions of proteins include agglomerated proteins and the concentration of these agglomerated proteins. Furthermore, where these preparations are made for consumer use, consumer appeal is of greater concern, which means that the preparation may need to have uniform, aesthetically pleasing, and reproducible qualities. Another example where homogeneously-sized particles with a certain, minimized concentration of agglomerates are valued is in the manufacture of toner compositions used in laser printers and photocopy machines. Toner products that have significant concentrations of agglomerates or large particles can cause defects in the printed materials and can also damage printers and photocopy machines. As in the case of CMP slurries, the art relevant to the manufacture of pharmaceuticals and toner products has attempted to address the need to minimize large particles by improving milling and mixing procedures and employing filters.

But, despite attempts to address the need to characterize large particles in a solution predominantly composed of uniformly-sized fine (smaller) particles, there remain inefficiencies in the art. And those inefficiencies can affect manufacturing processes (e.g., semiconductor manufacturing and pharmaceutical manufacturing) in undesired ways. Accordingly, there remains a need to more efficiently detect and characterize large particles in suspensions predominantly composed of uniformly-sized fine (smaller) particles.

SUMMARY

Disclosed herein is a method of characterizing large particles present among a mixture of particles more highly concentrated with small particles. The method generally includes preparing a suspension of the mixture in an electrolyte. The method further includes passing the prepared suspension, and a plurality of the particles therein, through an aperture of a device capable of characterizing particles according to the Coulter principle to obtain data on the particles. Still further, the method includes deriving a particle size distribution from the obtained data. The suspension includes at least one small particle per aperture volume. The large particles have an average diameter that is at least five times greater than the average diameter of the small particles. The aperture has a diameter that is (i) at least 50 times greater than the average diameter of the small particles, and (ii) about 1.2 times greater than the average diameter of the large particles to less than about 50 times greater than the average diameter of the large particles.

The method advantageously employs a device capable of characterizing particles according to the Coulter principle. Thus, no special equipment beyond what is presently commercially available is necessary to perform the disclosed method. Furthermore, the disclosed method is particularly useful because it provides a particle characterization method that avoids or reduces problems attendant with conventional methods, such as complicated and cumbersome dilutions and inaccurate reporting resulting from the sparse data gathered from particles that occur infrequently in the sample being characterized. With the disclosed method, it is now possible to more efficiently detect and characterize large particles present in a variety of compositions such as, for example, chemical mechanical polishing slurries, food emulsions, paints, pharmaceutical preparations, and toners for printers and photocopy machines.

Additional features of the invention may become apparent to those skilled in the art from a review of the following detailed description, taken in conjunction with the drawings, the examples, and the appended claims.

BRIEF DESCRIPTION OF THE DRAWING FIGURES

For a more complete understanding of the disclosure, reference should be made to the following detailed description and accompanying drawing wherein.

While the disclosed method is susceptible of embodiments in various forms, there are illustrated in the drawings (and will hereafter be described) specific embodiments of the invention, with the understanding that the disclosure is intended to be illustrative, and is not intended to limit the invention to the specific embodiments described and illustrated herein.

DETAILED DESCRIPTION

The background discussion, above, identifies the importance in various arts of characterizing large particles that might be present in a suspension predominantly composed of uniformly-sized fine (smaller) particles. The large particles may be formed by agglomeration or polymerization, or may be residual particles resulting from defective or imperfect milling or formation methods. Particles can be non-biological or biological. Non-biological particles can include, for example, abrasives used in chemical mechanical planarization, metal particles, latex particles, and silica particles. Biological particles can include, for example, cells, proteins, starch grains, and other aggregates of biological polymers. Disclosed herein is a method that provides these arts with the ability to accurately and efficiently detect and characterize large particles present among a mixture of particles more highly concentrated with small particles. The method employs a device capable of characterizing particles according to the Coulter principle. Indeed, a conventional apparatus capable of characterizing particles according to the Coulter principle may be used to carry out the disclosed method. Conventional application of such apparatus and the Coulter principle, however, are not necessarily suitable to address the needs in the art.

In conventional applications, the apparatus would draw particles suspended in an electrolyte solution through a small aperture, one particle at a time. The aperture is located between two electrodes that have an electric current flowing between them, which creates a sensing zone. As a particle passes through the aperture (or sensing zone), it displaces its own volume of electrolyte, momentarily changing the impedance between the two electrodes. This sudden change in impedance produces a momentary signal that can be measured and digitally processed. In conventional applications, when characterizing a mixture of large and small particles, an aperture diameter is selected that produces a signal that is discernible from the background when either a small or large particle passes through it. The signal is related to the volume of the particle that produced it, and as a result, a size distribution of number, volume, and surface area of the particles in suspension can be obtained from analysis of such data. In addition, if a known volume of the particle suspension is drawn through the aperture, the concentration of particles in the suspension can be obtained. The time required for such characterizations is typically about 3 minutes, and is limited to about 30 minutes due to undesirable particle settling and aggregation. Due to these time constraints, the conventional application has limitations that, left unaddressed, can lead to erroneous characterizations and statistical sampling errors.

One such erroneous characterization is referred to as the coincidence effect, which occurs when several particles pass through the aperture simultaneously. The magnitude of the change in impedance produced by multiple particles within the aperture at the same moment results in errors in the calculated particle size distribution, making it appear that there are larger particles in the sample than are actually present. As the concentration of particles increases, the probability of multiple particles passing through the aperture simultaneously increases sharply. The coincidence effect, and the concomitant erroneous characterizations, are generally avoided by sufficiently decreasing the concentration of the particles in the electrolyte such that only one particle will pass through the aperture at a time. Depending upon the concentration of the starting sample and to avoid this error, for example, dilutions up to 5,000- to 100,000-fold or more are not uncommon.

Dilution, however, can result in statistical sampling errors. For example, in a sample that contains a high concentration of small particles and a low concentration of large particles, dilution can result in significant sampling errors in counting the relatively scarce large particles. These errors can result in either over-reporting or under-reporting of the large particles. Over-reporting occurs when, due to sampling error, the large particles are over sampled and the reported concentration of large particles is much higher than the actual concentration. Similarly, under-reporting occurs when the large particles are under sampled and the reported concentration of large particles is much lower than the actual concentration. This over- and under-reporting problem is amplified as the dilution factor increases. Larger volumes of highly diluted samples can be characterized by performing multiple tests on the diluted sample, either sequentially on the same instrument or in parallel on multiple instruments. Such approaches, however, inevitably introduce additional sources of experimental error in the form of run-to-run variation and instrument-to-instrument variation.

The conventional application of the Coulter principle described above is not well-suited to detect the presence of large particles in CMP slurries, for example. Such slurries typically contain billions of uniformly-sized small particles per milliliter of liquid. At such high concentrations, these particles would inevitably implicate the coincidence effect known to occur when several particles pass through the aperture simultaneously. As noted above, the coincidence effect is generally avoided by decreasing the concentration of the particles (i.e., by diluting the sample) to the point that only one particle will pass through the aperture at a time. Such dilutions, however, can lead to the sampling errors described above. More importantly, such dilutions may be entirely undesired where, for example, the solution sought to be characterized needs to be used for its intended purpose (e.g., as a slurry in a CMP application) and not destroyed simply for a quality control analysis. Furthermore, extensive dilutions can lead to undesirable settling or aggregation because of the long characterization times associated with large volumes.

In addition to characterizing CMP slurries, the disclosed method may be useful in characterizing solutions containing proteins. Proteins in solution may have a tendency to agglomerate. Therefore, protein solutions can include relatively rare large protein agglomerates and relatively high concentrations of non-agglomerated (smaller) proteins.

The method disclosed herein provides the art with the ability to quickly characterize large particles present among a mixture of particles more highly concentrated with small particles. The method employs a device capable of characterizing particles according to the Coulter principle, yet desirably avoids the coincidence effect and avoids the extensive dilutions often necessary according to conventional applications of the Coulter principle. More specifically, the disclosed method generally includes preparing a suspension of the mixture in an electrolyte. The method further includes passing the prepared suspension, and a plurality of the particles therein, through an aperture of a device capable of characterizing particles according to the Coulter principle to obtain data on the particles. Still further, the method includes deriving a particle size distribution of the large particles from the obtained data.

The suspension includes at least one small particle per aperture volume. Preferably, the suspension includes at least 30 small particles per aperture volume, and even more preferably at least 400 particles per aperture volume, and still more preferably at least 3100 particles per aperture volume.

The large particles have an average diameter that is at least five times greater than the average diameter of the small particles. Alternatively, the large particles may have an average diameter that is at least 10 times, 20 times, or 50 times greater than the average diameter of the small particles.

The diameter of the aperture is selected so that the large particles are within the effective measuring range and the small particles are outside the effective measuring range. The aperture has a diameter that is (i) at least 50 times greater than the average diameter of the small particles, and (ii) about 1.2 times greater than the average diameter of the large particles to less than about 50 times greater than the average diameter of the large particles. Alternatively, the aperture has a diameter that is about 5 to about 40 times, about 10 to about 30 times, or about 15 to about 25 times greater than the average diameter of the large particles.

The disclosed method also preferably provides the art with the ability to characterize differently-sized large particles present among a mixture of particles more highly concentrated with small particles. Specifically, the large particles can include first and second collections of large particles, each such collection defined by particles having a consistent average size. For example, and according to one embodiment, the first collection of large particles can have an average diameter that is at least five times greater than the average diameter of the small particles, and the second collection of the large particles can have an average diameter that is at least 2.5 times greater than the average diameter of the first collection of large particles. In an alternative embodiment, the average diameter of the second collection of the large particles is at least 5 times greater than the average diameter of the first collection of large particles. In another alternative embodiment, the average diameter of the second collection of the large particles is at least 10 times greater than the average diameter of the first collection of large particles. Additional collections of large particles may be present and capable of characterization according to the disclosed method. The method is sufficiently flexible to characterize the presence of differently-sized large particles that might be present in a mixture more highly concentrated with uniformly-sized small particles.

According to embodiments of the disclosed method, it is possible to more accurately and efficiently detect and characterize large particles present in, for example, a chemical mechanical polishing slurry. With such characterization, a semiconductor manufacturer can take steps necessary to remove the large particles from the slurry before the slurry is used to polish a wafer, or consider using a different slurry altogether. Accordingly, the semiconductor manufacturer is able to better avoid the potential that the slurry could scratch the wafer or otherwise polish the wafer in a non-uniform manner. Furthermore, the disclosed method can be performed with conventional equipment. Still further, the manufacturer need not employ cumbersome dilution techniques to utilize the equipment. Similarly, the disclosed method makes it possible to more accurately and efficiently detect and characterize large particles present in a variety of other compositions where a minimized concentration of large particles is desirable such as, for example, in the manufacture of food emulsions, pharmaceutical preparations, paints, and toners for printers and photocopy machines.

The disclosed method achieves its fullest advantage when the large particles are present in the sample in trace amounts compared to the concentration of the small particles or, in other words, the large particles are present among a mixture of particles more highly concentrated with small particles. Accordingly, the concentration of the small particles is preferably at least 10 times that of the larger particles. More preferably, the concentration of the small particles is at least 1,000 times that of the larger particles. Even more preferably, the concentration of the small particles is at least 100,000 times that of the larger particles.

As used herein, the adjectives "large" and "small" and variations thereof used to define the particles are references to the diameter of a collection of similarly sized particles. Thus, for example, if a mixture is designed and intended to contain particles having a diameter of 0.1 micrometers (µm), such particles can be considered "small" particles, whereas particles in the same mixture having a diameter of 0.5 µm or greater would be considered "large" particles.

It can be difficult, impractical, or otherwise unnecessary to specify with precision the actual diameter of each and every particle. For purposes of the disclosed method, however, it is not necessary to define particles with such precision. Therefore, as used herein, the term "average diameter" is intended to define the average diameter of particles one might classify as large or small, or otherwise classify into a sub-collection of large and small particles. Where such precise measurements are known, possible, or practical, and the particles can be classified with such precision, the "average" diameter of such particles may, of course, more closely coincide with the actual diameter.

Figures 1, 1A:
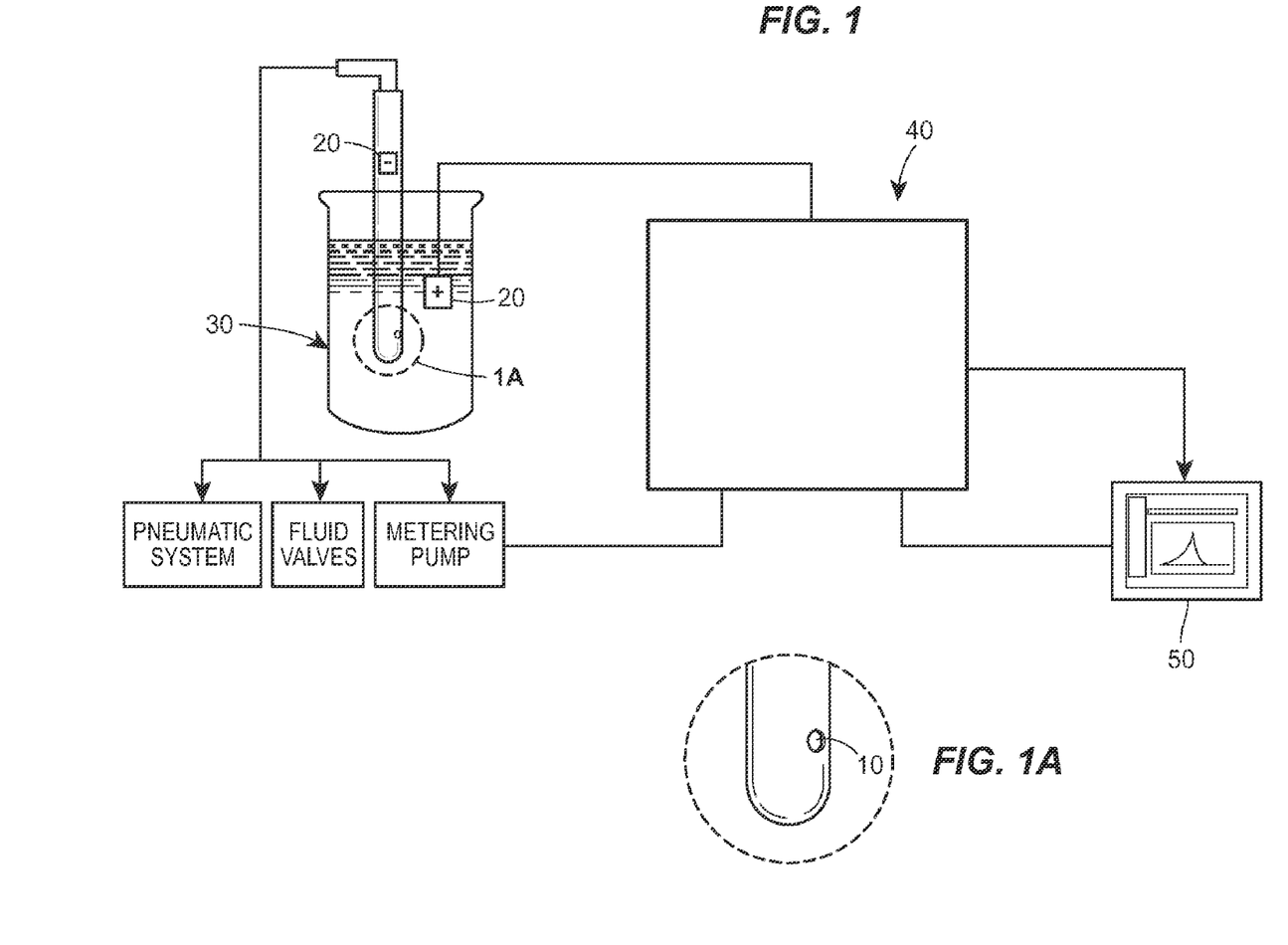
FIG. 1 is a schematic of a Coulter apparatus, including a detector and an aperture therein.
FIG. 1A is an exploded view of the aperture.

With reference to FIG. 1, a sample containing small and large particles may be suspended in an appropriate electrolyte solution to obtain a sample solution 30. See ISO 13319: Determination of particle size distributions—Electrical sensing zone methods, Annex A.2, 2000 (Materials and recommended electrolyte solutions). A current flows between electrodes to create a sensing zone defined by an aperture 10. The sample solution 30 passes through the aperture 10. Particles in the sample solution 30 passing through the aperture 10 displace a corresponding volume of electrolyte, momentarily changing the impedance between the electrodes 20. A detector 40 measures this transient change in impedance, which is recorded by a computer 50 as a pulse that can be converted to useful data.

Apertures are available in a range of diameters such as, for example, a range of about 20 µm to about 2000 µm. In accordance with the disclosed method, the aperture is selected so that the small particles in the sample solution are outside an effective measuring range of the aperture. Surprisingly, when the small particles are outside the effective measuring range of the aperture, the small particles do not interfere with accurate characterization of the large particles. The effective measuring range of an aperture is generally about 2% to about 80% of the aperture diameter. Thus, for example, the effective measuring range for an aperture having a diameter of 50 µm is 1 µm (2% of 50) to 40 µm (80% of 50). Typical effective measuring ranges are, for example, set out in the Table, below. Typical aperture volumes are also, for example, set out in the Table, below.

TABLE

Typical Effective Measuring Ranges and Aperture Diameters

| Effective Measuring Range (μm) | Aperture Diameter (μm) | Aperture Volume (pL) |
|---|---|---|
| 0.4 to 16 | 20 | 9 |
| 1 to 40 | 50 | 69 |
| 2 to 80 | 100 | 550 |
| 4 to 160 | 200 | 4400 |
| 8 to 320 | 400 | 35,000 |
| 20 to 800 | 1000 | 550,000 |

Because apertures are prone to blockage by large particles, preferred embodiments of the disclosed method will include the use of an effective measuring range that is from about 2% to about 60% of the aperture diameter.

Conventional application of the Coulter principle, however, would teach to select an aperture diameter that is capable of measuring both the small particles and the large particles, because such applications are typically employed to accurately count or otherwise characterize all of the particles in the mixture. In the context of the present method, however, data related to the small particles is not necessarily pertinent and, therefore, aperture diameter is not best selected according to the conventional application of the Coulter principle.

Benefits of the disclosed method are evident from the following hypothetical comparison, with reference to the foregoing Table. Suppose a sample contains small particles having an average diameter of 1.5 μm and trace amounts of large particles having an average diameter of 20 μm. According to conventional application of the Coulter principle and conventional apparatus, the sample would be diluted to such an extent that only one particle of either size would be present in the aperture at a time, and an aperture with a diameter of 50 μm would be selected so that the apparatus would detect both the large and small particles. In contrast to the conventional applications, under the disclosed method, an aperture with a diameter of 100 μm could be selected because that aperture would effectively measure the large particles, but not the small particles. Further, the sample would require substantially less dilution (if any) than necessitated by the conventional application, permitting characterization of a statistically valid number of large particles in less time. The disclosed method can reduce the dilution of the sample required according to conventional application of the Coulter principle, by a factor of about 10-fold to about 100-fold, or eliminate dilution altogether.

The volume of the aperture can be calculated based on the dimensions of the aperture. Apertures are generally cylindrical in shape, although other shapes are possible. Generally, for cylindrical apertures, the depth of the aperture varies with the diameter. Therefore, an aperture with a smaller diameter will have a smaller depth, and an aperture with a larger diameter will have a larger depth.

Using the disclosed method it has been found, surprisingly, that at a higher particle concentration than would normally be acceptable in samples containing small and large particles, large particles can be characterized accurately. Specifically, the method disclosed herein allows for the characterization of a large particle in the presence of small particles in the aperture.

According to further embodiments, in addition to the selection of an aperture with an effective measuring range that is greater than the diameter of the small particles, a detection threshold, such as a measurement threshold current, can be established on the detection instrument. The detection threshold can be selected so that the instrument response generated by the small particles falls below the detection threshold and, subsequently, does not interfere with characterization of the large particles.

The disclosed method can optionally include obtaining a background measurement of a suspension containing only the small particles and the electrolyte solution. This background measurement can be subtracted from the sample solution measurement to obtain a large particle measurement.

The disclosed method employs the Coulter principle to characterize particles, yet avoids or reduces the problems attendant with conventional applications of the Coulter principle, such as complex and cumbersome dilutions and over- and under-detection of the particles being characterized due to the resulting statistical sampling errors. Surprisingly, according to the disclosed method, the presence of several small particles in the aperture does not interfere with accurate characterization of large particles.

EXAMPLES

The following examples are provided to illustrate the invention, but are not intended to limit the scope thereof. Example 1 generally demonstrates the disclosed method is capable of characterizing large-diameter particles present in a solution that contains a higher concentration of small-diameter particles. Example 2 generally demonstrates that the disclosed method can not only characterize large particles present in a suspension containing predominantly smaller particles, but can simultaneously characterize differently-sized large particles present in a suspension containing predominantly smaller particles. Example 3 demonstrates that the statistical sampling error—the variance—and the differences in results between multiple runs of the same sample can be reduced by reducing dilutions.

Example 1

This example demonstrates that the disclosed method is capable of characterizing large-diameter particles present in a suspension more highly-concentrated with small-diameter particles.

Four sample solutions, each containing large- and small-size particles suspended in an electrolyte (ISOTON® II Diluent, commercially available from Beckman Coulter, Fullerton, Calif.), were prepared and then analyzed according to an embodiment of the disclosed method. Each sample solution included the same concentration of small polystyrene latex (PSL) particles having a diameter of 0.1 μm: $4.5 \times 10^{10}$ small particles per mL of electrolyte. Each of the four samples contained a different concentration of large PSL particles having a diameter of 1.2 μm. Thus, the ratio of the diameter of the large particle to that of the small particle in each sample was 12.

A first sample solution also contained 15,000 large particles per mL of electrolyte. Thus, this sample has a 3 million-times higher concentration of the small (0.1 μm) particles than the large (1.2 μm) particles.

A second sample solution also contained 60,000 large particles per mL of electrolyte. Thus, this sample has a 750,000-times higher concentration of the small (0.1 μm) particles than the large (1.2 μm) particles.

A third sample solution also contained 150,000 large particles per mL of electrolyte. Thus, this sample has a 300,000-times higher concentration of the small (0.1 μm) particles than the large (1.2 μm) particles.

A fourth sample solution also contained 300,000 large particles per mL of electrolyte. Thus, this sample has a 150,000-times higher concentration of the small (0.1 µm) particles than the large (1.2 µm) particles.

Each of the four samples was analyzed in a Beckman Coulter Multisizer™ 3 Coulter Counter® device (commercially available from Beckman Coulter, Fullerton, Calif.). The device employed an aperture that had a diameter of 20 µm, with an aperture volume of 9 pL. With $4.5 \times 10^{10}$ small particles per mL, the suspension for these experiments included about 400 small particles per aperture volume. The measurement threshold current was set at 400 micro amps (µA), and the gain was set at 8. The run time for the samples was about 70 seconds.

Figure 2:
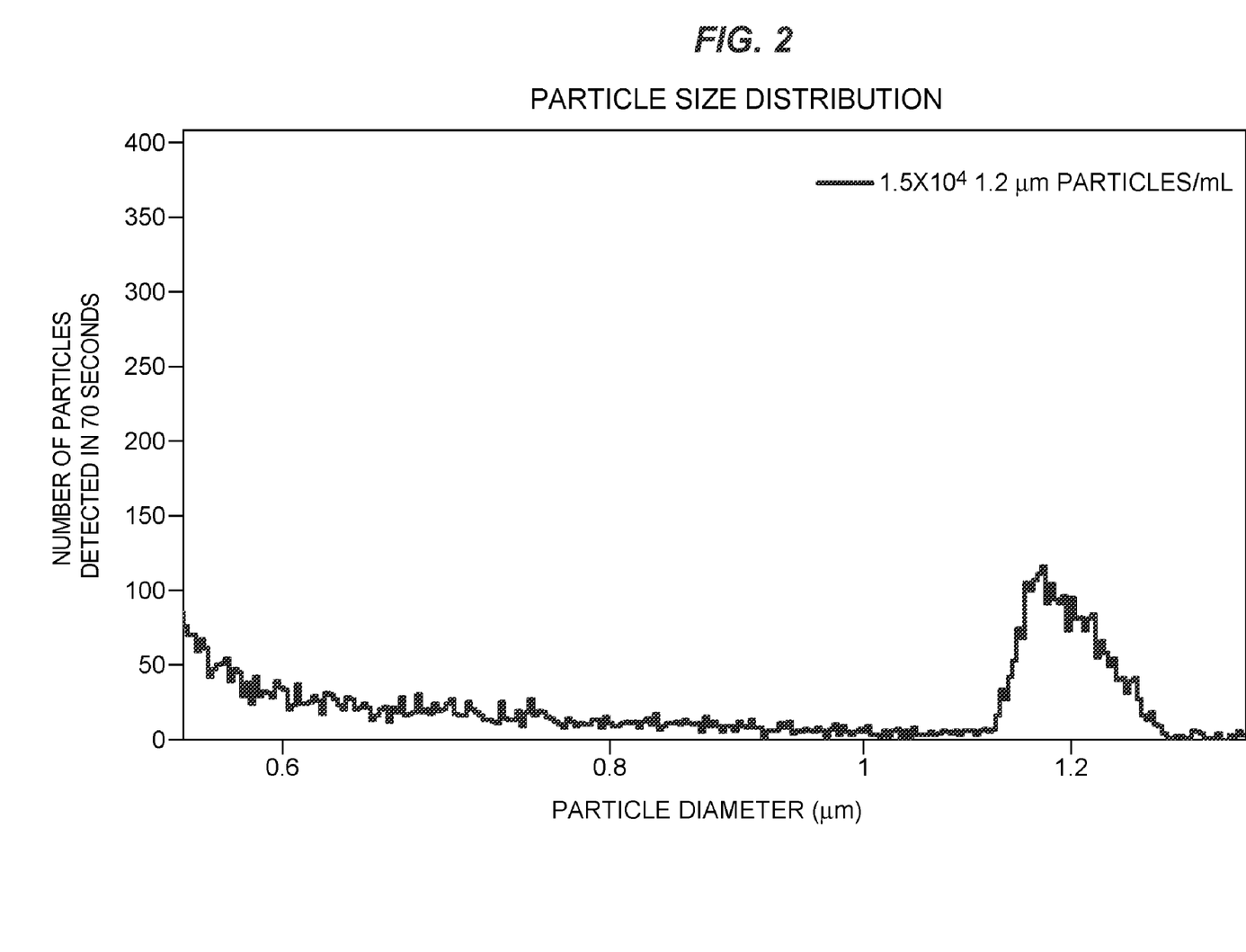
FIGS. 2-8 are graphs that illustrate particle size distribution (i.e., the number of particles as a function of the particle size) of particles present in the samples described in the Examples.

The device characterized the particles present in each sample. FIG. 2 presents the particle size distribution (i.e., the number of particles as a function of the particle size) of the particles present in the first sample solution (15,000 large particles per mL of electrolyte). As shown in FIG. 2, the employed method characterized the presence of the large particles. Specifically, the peak height associated with the large particle (1.2 µm) is proportional to the large particle concentration, despite the presence of up to a 3,000,000-times higher concentration of small particles (0.1 µm).

Figure 3:
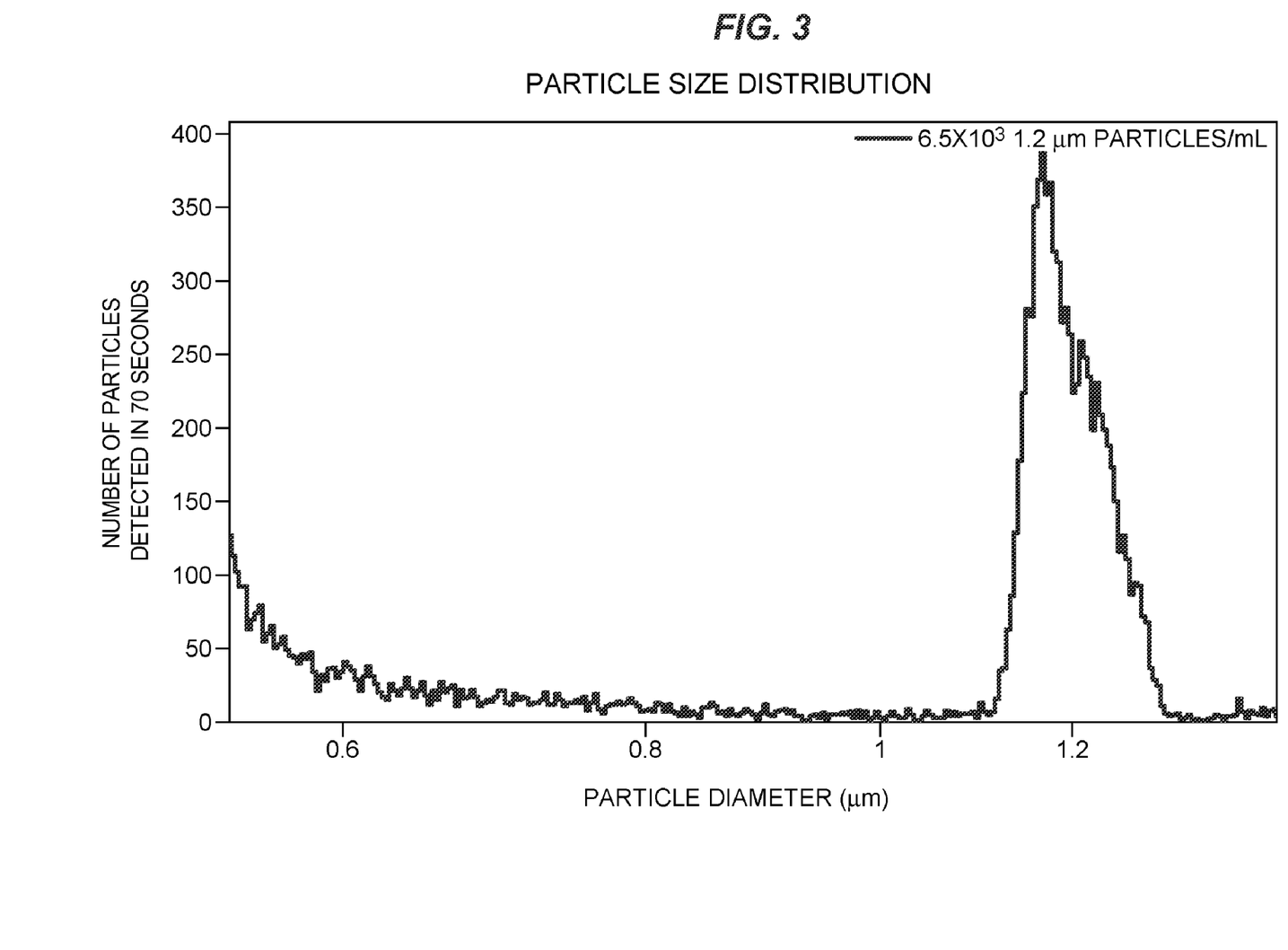

FIG. 3 presents the particle size distribution (i.e., the number of particles as a function of the particle size) of the particles present in the second sample solution (containing 60,000 large particles per mL of electrolyte). As shown in FIG. 3, the employed method characterized the presence of the large particles. Specifically, the peak height associated with the large particle (1.2 µm) is proportional to the large particle concentration, despite the presence of up to a 750,000-times higher concentration of small particles (0.1 µm).

Figure 4:
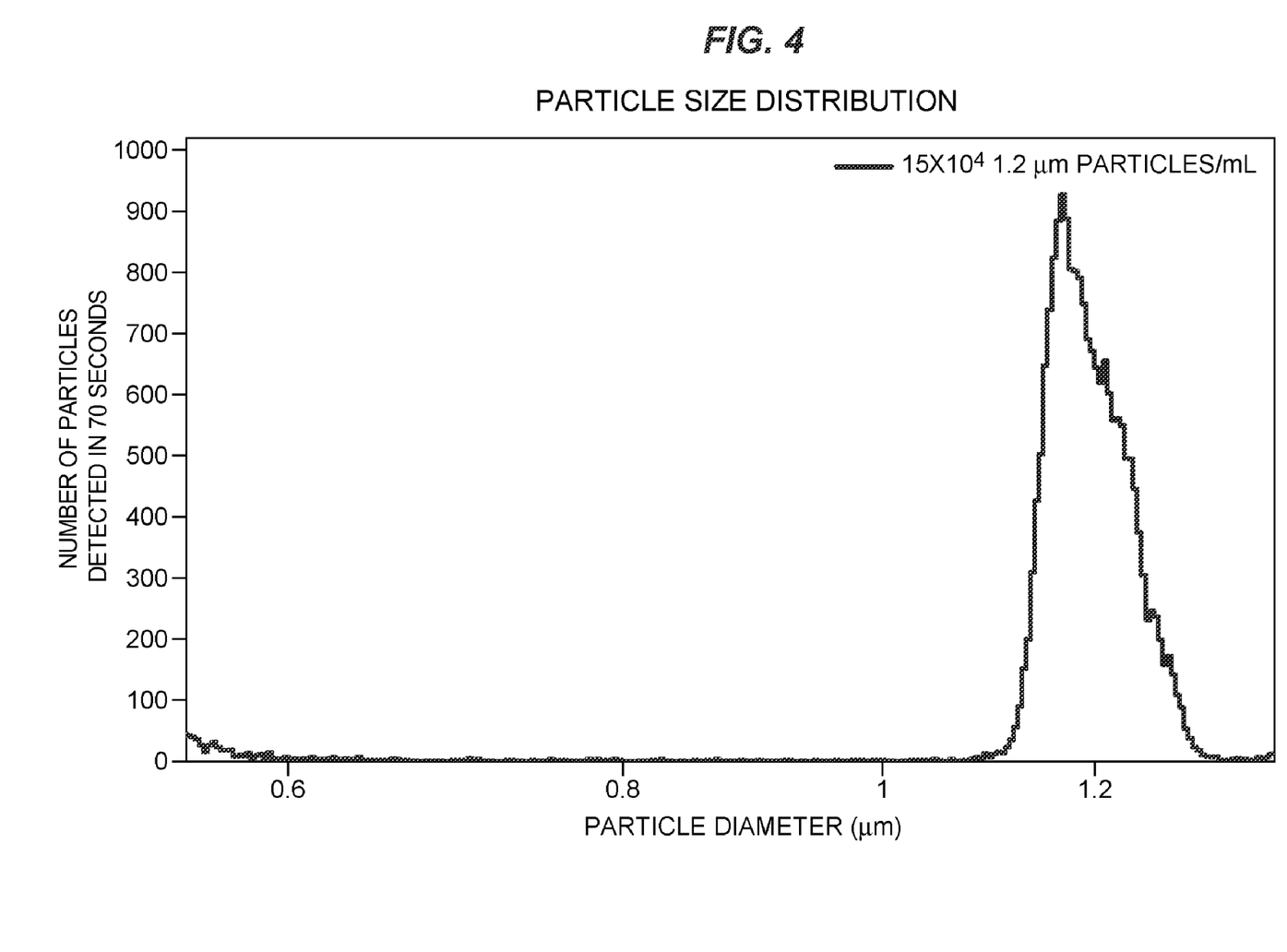

FIG. 4 presents the particle size distribution (i.e., the number of particles as a function of the particle size) of the particles present in the third sample solution (containing 150,000 large particles per mL of electrolyte). As shown in FIG. 4, the employed method characterized the presence of the large particles. Specifically, the peak height associated with the large particle (1.2 µm) is proportional to the large particle concentration, despite the presence of up to a 300,000-times higher concentration of small particles (0.1 µm).

Figure 5:
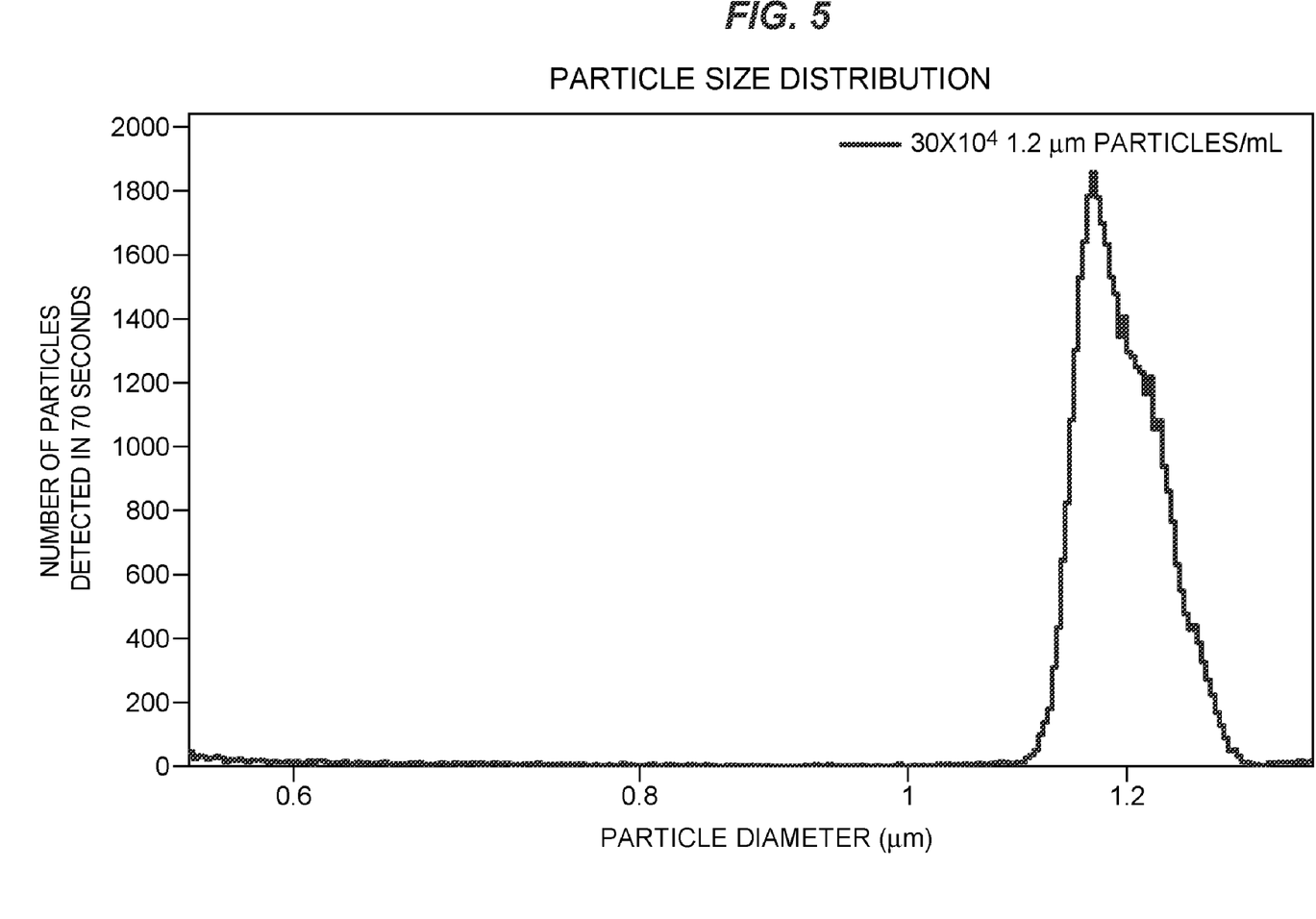

FIG. 5 presents the particle size distribution (i.e., the number of particles as a function of the particle size) of the particles present in the fourth sample solution (containing 300,000 large particles per mL of electrolyte). As shown in FIG. 5, the employed method characterized the presence of the large particles. Specifically, the peak height associated with the large particle (1.2 µm) is proportional to the large particle concentration, despite the presence of up to a 150,000-times higher concentration of small particles (0.1 µm).

Because the volume of sample passing through the aperture during the measurement is known from the measurement conditions, the particle size distribution, in combination with the dilution factor, allows calculation of the concentration of large particles in the sample. Accordingly, this example demonstrates that the employed method can characterize large particles present in a suspension containing predominantly—e.g., 300,000-times to 3,000,000-times higher concentration of—smaller particles in as little as about 70 seconds.

Example 2

This example demonstrates that the disclosed method can not only characterize large particles present in a suspension containing predominantly smaller particles, but can simultaneously characterize differently-sized large particles present in a suspension containing predominantly smaller particles.

Two sample solutions, each containing large- and small-size particles suspended in an electrolyte (ISOTON® II Diluent), were prepared and then analyzed according to an embodiment of the disclosed method. Each sample solution included the same concentration of small PSL particles having a diameter of 0.1 µm: $4.5 \times 10^{10}$ small particles per mL of electrolyte.

A first sample solution also contained 1000 particles per mL of electrolyte, wherein the particles had a diameter of 2 µm. Thus, the ratio of the diameter of this larger particle (2 µm) to that of the small particle (0.1 µm) was 20. Furthermore, the solution contained 45 million-times more small particles (0.1 µm) than the large particles (2 µm).

A second sample solution similarly also contained 1000 particles per mL of electrolyte, wherein the particles had a diameter of 2 µm (and, therefore, the ratio of the diameter of this particle (2 µm) to that of the small particle (0.1 µm) was similarly 20). The second sample solution, however, further contained 700 PSL particles each having a diameter of 5 µm (the ratio of the diameter of this particle (5 µm) to that of the small particle (0.1 µm) was 50). Like the first sample solution, this second sample solution contained 45 million-times more small particles than the 2 µm-size particles. Furthermore, this second sample solution contained more than 64 million-times more small particles than the 5 µm-size particles.

The two sample solutions were analyzed in the same manner as described in Example 1, above, except that the diameter of the aperture was 50 µm, with an aperture volume of 69 pL. With $4.5 \times 10^{10}$ small particles per mL, the suspension for these experiments included about 3100 small particles per aperture volume. The measurement threshold current was set at 800 µA, and the gain was set at 8. The run time for the samples was about 102 seconds.

Figure 6:
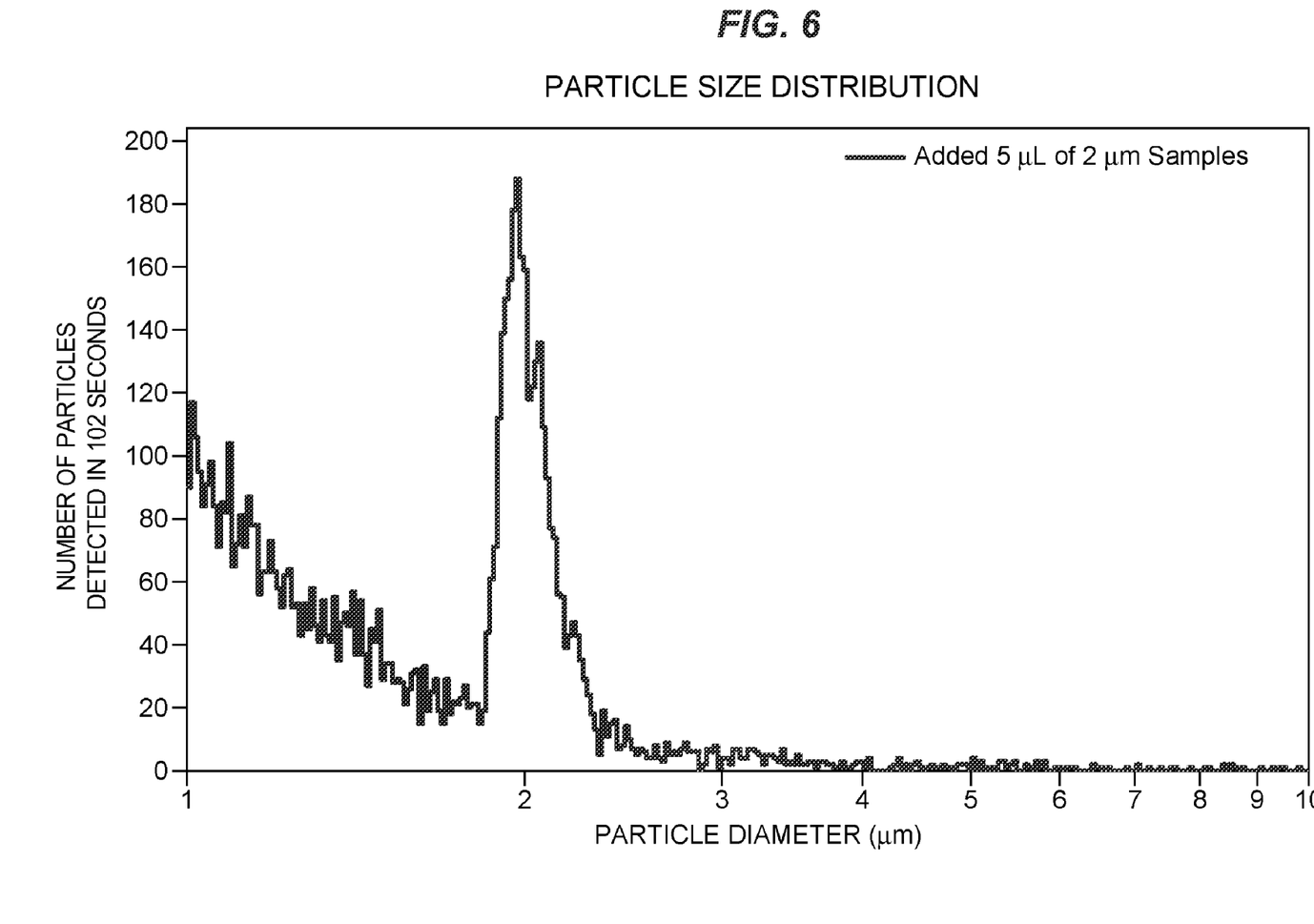

FIG. 6 presents the particle size distribution (i.e., the number of particles as a function of the particle size) of the particles present in the first sample solution (containing 1000 of the 2 µm-size particles per mL of electrolyte). As shown in FIG. 6, the employed method characterized the presence of the 2 µm-size particles. Specifically, the peak height associated with the 2 µm-size particle is proportional to the 2 µm-size particle concentration, despite the presence of up to a 45 million-times higher concentration of small particles (0.1 µm).

Figure 7:
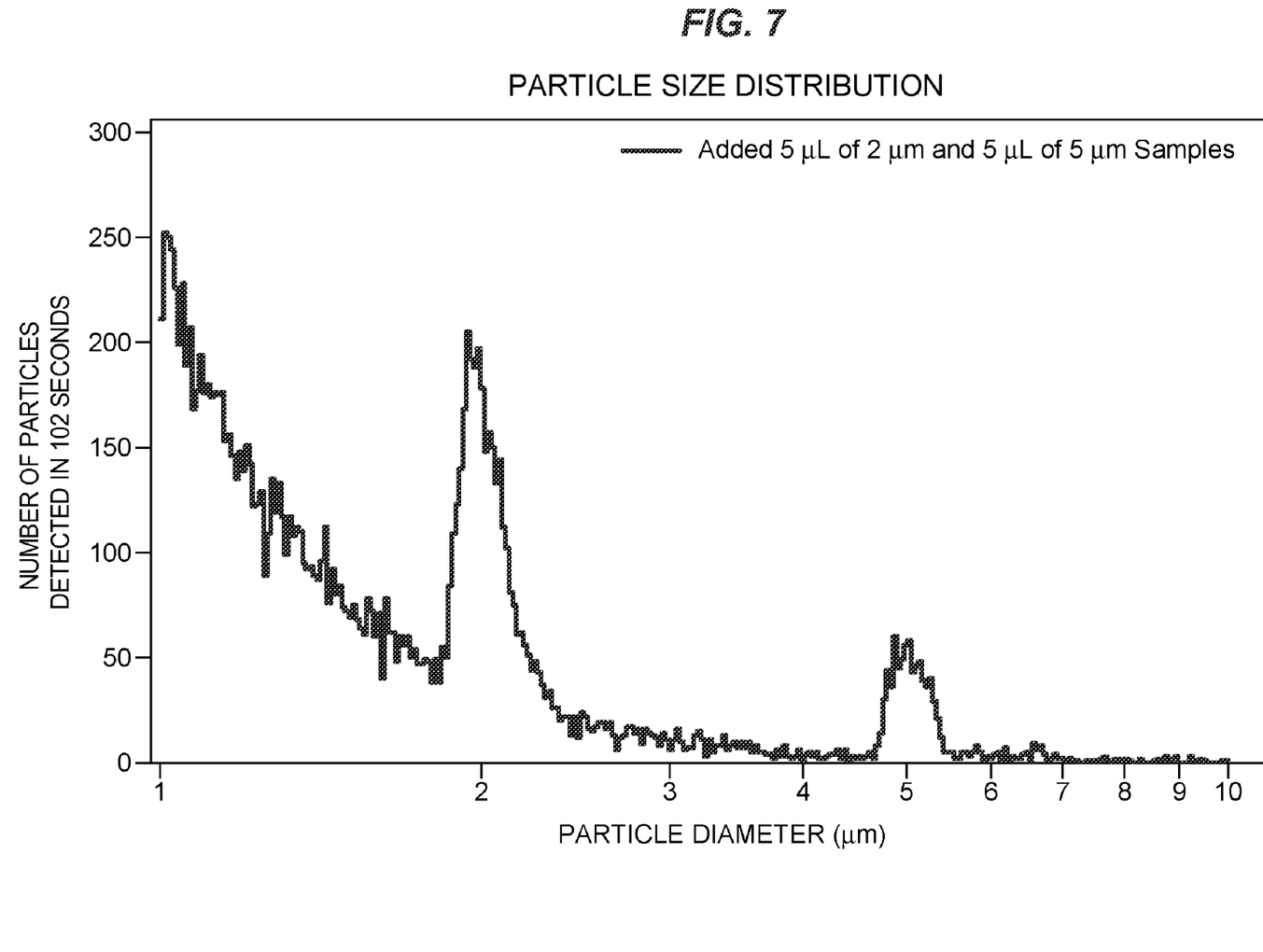

FIG. 7 presents the particle size distribution (i.e., the number of particles as a function of the particle size) of the particles present in the second sample solution (containing 1000 of the 2 µm-size particles per mL of electrolyte, and containing 700 of the 5 µm-size particles per mL of electrolyte). As shown in FIG. 7, the employed method characterized the presence of both the 2 µm-size particles and the 5 µm-size particles. Specifically, the peak heights associated with the 2 µm-size particle and the 5 µm-size particle particles are proportional to the concentration of each, despite the presence of up to a 45 million-times higher concentration of small particles (0.1 µm) relative to the 2 µm-size particles and a greater than 64 million-times higher concentration of small particles (0.1 µm) relative to the 5 µm-size particles.

Because the volume of sample passing through the aperture during the measurement is known from the measurement conditions, the particle size distribution, in combination with the dilution factor, allows calculation of the concentration of differently-sized large particles in the sample. Accordingly, this example demonstrates that the employed method can not only characterize large particles present in a suspension containing predominantly—e.g., 45 million-times higher concentration of—smaller particles, but can simultaneously characterize differently-sized large particles (2 µm-size particles and 5 µm-size particles) present in a suspension containing predominantly smaller particles (0.1 µm-size particles).

Example 3

A sample solution containing large- and small-size particles suspended in an electrolyte (ISOTON® II Diluent), was prepared and then analyzed according to a conventional method of counting particles. Specifically, the sample solution included the following concentration of small PSL particles having a diameter of 0.1 μm: $4.5 \times 10^{10}$ small particles per mL of electrolyte. That solution also included a trace amount (approximately 1100 particles per mL) of a large PSL particle having a diameter of 5 μm. Thus, this sample has a 40 million-times higher concentration of the small (0.1 μm) particles than the large (5 μm) particles.

The sample solution was twice analyzed in the same manner as described in Example 1, above, except that the diameter of the aperture was 50 μm, with an aperture volume of 69 pL. With $4.5 \times 10^{10}$ small particles per mL, the suspension included about 3100 small particles per aperture volume. The measurement threshold current was set at 800 μA. The run time for the samples was about 206 seconds.

Figure 8:
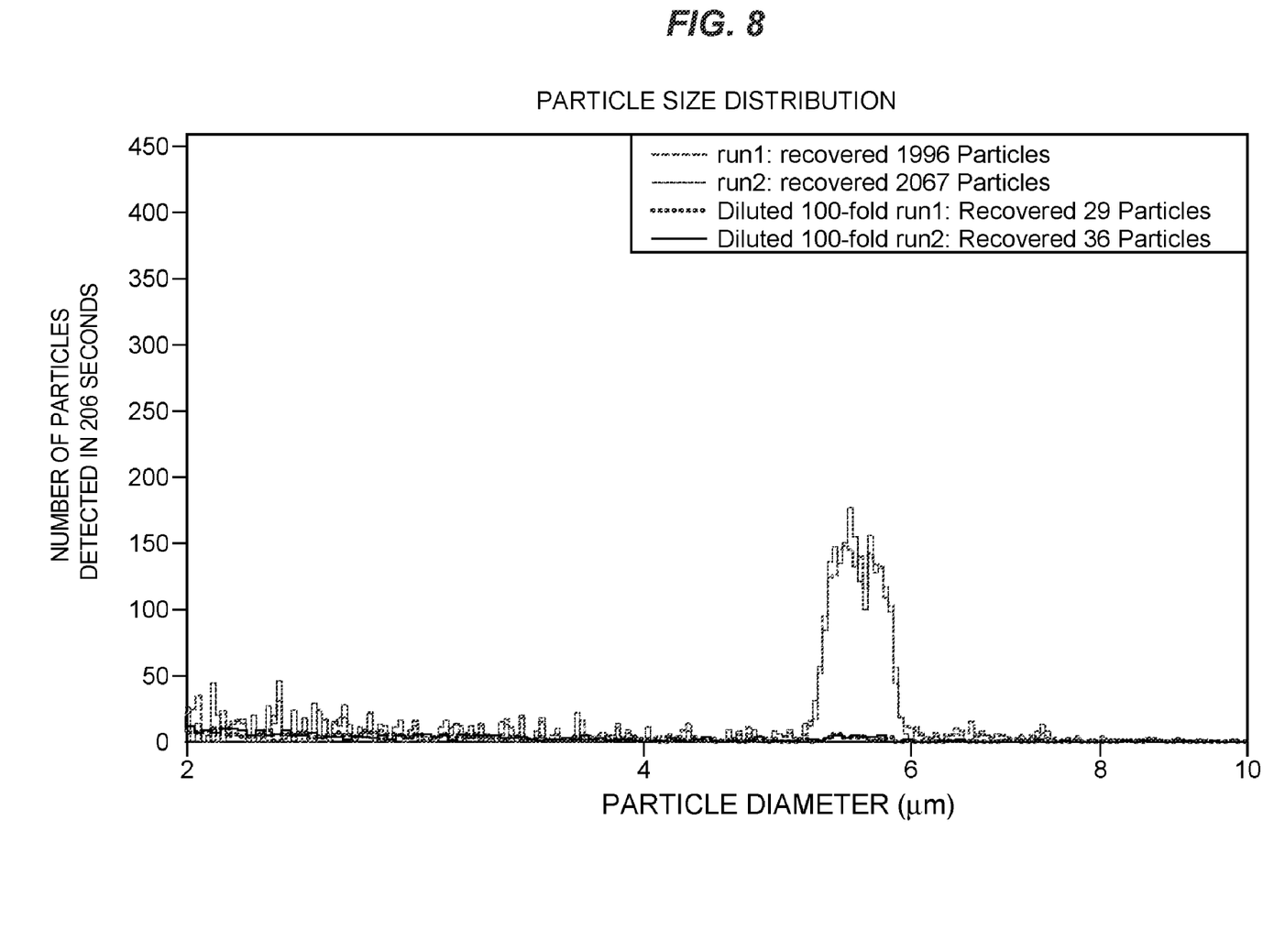

FIG. 8 presents the particle size distribution (i.e., the number of particles as a function of the particle size) of the particles present in each analysis of the same sample solution, the first analysis identified in the figure as "run 1," and the second as "run 2." Based on the obtained data, "run 1" counted 1996 of the 5 μm-size particles, while "run 2" counted 2067 such particles, with a variance of 2.5%.

The sample was thereafter diluted 100-fold to test the accuracy of counting particles in diluted samples. With $4.5 \times 10^8$ small particles per mL, the suspension for this dilution included about 31 small particles per aperture volume. The diluted sample was twice analyzed in the same manner as described relative to the undiluted sample.

FIG. 8 presents the particle size distribution of the particles present in each analysis of the same diluted sample solution, the first analysis identified as "diluted 100-fold run 1," and the second as "diluted 100-fold run 2." Based on the obtained data, "diluted 100-fold run 1" counted 29 of the 5 μm-size particles, while "diluted 100-fold run 2" counted 36 such particles, with a variance of 15%.

The data obtained in this example demonstrate that the statistical sampling error—the variance—and the differences in results between multiple runs of the same sample can be reduced by reducing the dilutions. In this instance, the sampling error (as shown by decreased reproducibility between runs) was increased by a factor of 6 with a 100-fold dilution. Therefore, sampling errors of this type will increase with further dilutions as required under the conventional method.

The foregoing examples demonstrate an effective method for characterizing large particles present in a solution more highly concentrated with small particles. The method achieves accurate particle characterization without the extensive dilution required by conventional particle characterization methods. The method also ensures that the particles are characterized without the errors or with a reduction of the errors associated with dilution.

The foregoing description is given for clarity of understanding only, and no unnecessary limitations should be understood therefrom, as modifications within the scope of the invention may be apparent to those having ordinary skill in the art.

What is claimed is:

1. A method of characterizing large particles present among a mixture of particles more highly concentrated with small particles, the method comprising:
   (a) preparing a suspension of the mixture in an electrolyte;
   (b) passing the prepared suspension, and a plurality of the particles therein, through an aperture of a device capable of characterizing particles according to the Coulter principle to obtain data on the particles; and,
   (c) deriving a particle size distribution from the obtained data, wherein the suspension comprises at least one small particle per aperture volume, and wherein the large particles have an average diameter that is at least five times greater than the average diameter of the small particles, and the aperture has a diameter that is (i) at least 50 times greater than the average diameter of the small particles, and (ii) about 1.2 times greater than the average diameter of the large particles to less than about 50 times greater than the average diameter of the large particles.

2. The method of claim 1, wherein the suspension comprises at least 30 small particles per aperture volume.

3. The method of claim 1, wherein the suspension comprises at least 400 small particles per aperture volume.

4. The method of claim 1, wherein the suspension comprises at least 3100 small particles per aperture volume.

5. The method of claim 1, wherein the large particles have an average diameter that is at least 10 times greater than the average diameter of the small particles.

6. The method of claim 1, wherein the large particles have an average diameter that is at least 20 times greater than the average diameter of the small particles.

7. The method of claim 1, wherein the large particles have an average diameter that is at least 50 times greater than the average diameter of the small particles.

8. The method of claim 1, wherein the aperture has a diameter that is about 5 to about 40 times greater than the average diameter of the large particles.

9. The method of claim 1, wherein the aperture has a diameter that is about 10 to about 30 times greater than the average diameter of the large particles.

10. The method of claim 1, wherein the aperture has a diameter that is about 15 to about 25 times greater than the average diameter of the large particles.

11. The method of claim 1, wherein the large particles comprise first and second collections of large particles, and wherein the first collection of large particles has an average diameter that is at least five times greater than the average diameter of the small particles, and the second collection of the large particles has an has an average diameter that is at least 2.5 times greater than the average diameter of the first collection of large particles.

12. The method of claim 11, wherein the average diameter of the second collection of the large particles is at least 5 times greater than the average diameter of the first collection of large particles.

13. The method of claim 11, wherein the average diameter of the second collection of the large particles is at least 10 times greater than the average diameter of the first collection of large particles.

14. The method of claim 1, wherein a concentration of small particles is at least ten times greater than a concentration of large particles.

15. The method of claim 1, wherein a concentration of small particles is at least 1,000 times greater than a concentration of large particles.

16. The method of claim 1, wherein a concentration of small particles is at least 100,000 times greater than a concentration of large particles.

* * * * *